United States Patent [19]

Roques et al.

[11] Patent Number: 5,190,921
[45] Date of Patent: Mar. 2, 1993

[54] AMINO ACIDS AND PEPTIDES HAVING A MODIFIED TYROSINE RESIDUE, THEIR PREPARATION AND THEIR APPLICATION AS MEDICAMENTS

[75] Inventors: Bernard P. Roques, St. Maurice; Isabelle Marseigne, Lyons; Bruno Charpentier, Valbonne, all of France

[73] Assignee: Institut National de La Sante et de La Recherche Medicale (INSERM), Paris Cedex, France

[21] Appl. No.: 825,294

[22] Filed: Jan. 24, 1992

Related U.S. Application Data

[63] Continuation of Ser. No. 383,008, Jul. 21, 1989, abandoned.

[30] Foreign Application Priority Data

Aug. 1, 1988 [JP] Japan .................... 63-10391

[51] Int. Cl.⁵ .................. A61K 37/02; C07K 5/08; C07K 5/10; C07K 7/06
[52] U.S. Cl. .................. 514/17; 514/18; 530/329; 530/330
[58] Field of Search .................. 514/17, 18; 530/329, 530/330

[56] References Cited

U.S. PATENT DOCUMENTS 4,657,899  4/1987  Rzeszotarski .................. 514/120

FOREIGN PATENT DOCUMENTS 0226217  6/1987  European Pat. Off.
0268297  5/1988  European Pat. Off.
2606018  5/1988  France.

OTHER PUBLICATIONS

Journal of Controlled Release, 13, 147-155, 1990.
Journal of Medicinal Chemistry, 32, 445-449, 1989.
Neurology Neurobiology, vol. 46, pp. 231-234, 1988.
Marseigna, J. Org. Chem., vol. 53, No. 15, pp. 3621-3624, Jul. 22, 1988.

Primary Examiner—Lester L. Lee
Attorney, Agent, or Firm—Jacobson, Price, Holman & Stern

[57] ABSTRACT

These compounds are represented by formula (I), in which each of $R_1$ and $R_2 =$ H, $C_1-C_8$ alkyl, $C_3-C_7$ cycloalkyl, or aromatic; (when $R_1 =$ H, $R_2$ can be an amine function-protecting radical, amino acid residue or peptide fragment; $R_1$ and $R_2$ being capable of forming, with N, a 5-7 component ring); A = carbonyl or methylene; W = hydroxy, phenoxy, $C_1-C_8$ alkoxy; phenoxy($C_1-C_8$ alkyl), amino, ($C_1-C_8$ alkyl)amino, di($C_1-C_8$ alkyl)amino, (when A = carbonyl, W = amino acid residue or peptide fragment); Y = —$OSO_2OR_3$(II), —$OPO(OR_3)_2$ (III), —$(CH_2(_m$—$SO_2OR_3$ (IV) or —$(CH_2)_m$—$PO(OR_3)_2$ (V) [$R_3 =$ H, $C_1-C_8$ alkyl; m = 1 to 4]; Z = cyclohexane, pyridyl or phenyl; n = 0 to 4; on the condition that when Y = (II) or (III), -A-W is other than a sequence composed of natural amino acids. They have antipsychotic properties, an effect facilitating the memorization processes, analgesic properties; they are useful as anorexia-producing agents, and they have stimulatory effects on intestinal motility.

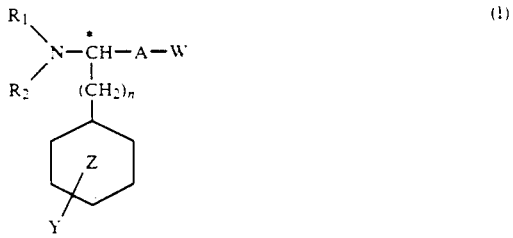

16 Claims, No Drawings

AMINO ACIDS AND PEPTIDES HAVING A MODIFIED TYROSINE RESIDUE, THEIR PREPARATION AND THEIR APPLICATION AS MEDICAMENTS

RELATED APPLICATION

This is a continuation of Ser. No. 383,008, filed Jul. 21, 1989 and now abandoned.

The present invention relates to new amino acids and their derivatives, as well as to new peptides. These new amino acids contain, in their formula, a modified tyrosine residue; while the new peptides contain, in their sequence, a modified tyrosine residue, with, in particular, a specific arrangement of amino acids.

The invention also relates to the preparation of these new compounds, as well as their application as medicaments, in particular in the treatment of nervous diseases of central origin.

The presence of a sulfated tyrosine residue has been demonstrated in many peptides (fibrinopeptide B [Bettelheim, F. R., J. Am. Chem. Soc., 76, 2838 (1954)], gastrin [Gregory, H. Nature, 204, 931 (1964)], cholecystokinin [Mutt, V., Eur. J. Biochem., 6, 156, (1968)]) and, more recently, in several secretory proteins (immunoglobulin G [Baeuerle, P. A., Embo J., 3, 2209 (1984)] and fibronectin [Liu, M. C., Proc. Natl. Acad. Sci. USA, 82, 34, (1985)]).

Sulfation of the phenolic —OH group of the amino acid tyrosine is in all likelihood a post-translation event which takes place at the tyrosine residues of pro-cholecystokinin [Vargas, F., Ann. NY Acad. Sci., 448, 110 (1985)]. This process could also occur in the case of the precursors of the encephalins, preproencephalin [Unsworth, C. D., Nature, 295, 519-522, (1982)]. Finally, sulfation of the amino acid tyrosine alone could also exist in biological media [Rondouin, G., Neuropept., 1, 23-28 (1980)].

The significance of sulfated tyrosine in biological processes is therefore obvious. However, the significance is limited by the fact that the —O—SO$_3$H bond is easily hydrolyzable [Bettelheim, F. R., J. Am. Chem. Soc., 76, 2838-2839, (1954)].

Another post-translation modification of proteins, which has been shown to be an important process in cellular regulation, is the phosphorylation of tyrosine residues [Hunter, T., Cell, 22, 647-648 (1980); Ushiro, H., J. Biol. Chem., 255, 8363-8365 (1980)]The phosphorylation of proteins, in particular membrane proteins (receptors, transducers, etc. . . . ), in fact takes place very particularly at the level of the tyrosine in peptide derivatives, under the action of enzymes called tyrosinekinases, certain of which will correspond to proteins expressed by oncogenes [Hunter, T., Ann. Rev. Biochem., 54, (1985), 897-930].

In addition, many agonists or antagonists of excitatory amino acid receptors have structures derived from the α-amino acids, characterized by an aliphatic side chain terminated by a sulfonic or phosphonic acid function [Watkins, J. C., Tins, 10(7), (1987), 265-272].

New amino acids have now been found, the potential significance of which as medicaments is as great as that of O-sulfated or O-phosphorylated tyrosine, but which have greater chemical stability and, as a consequence, are capable of having a longer period of action than O-sulfated or O-phosphorylated tyrosine when they are administered to a living organism.

The present invention also relates to new peptides having an O-sulfated or O-phosphorylated tyrosine residue capable of being modified, as in the case of the new amino acids of the invention, and comprising a specific arrangement of amino acids, through which they are also capable, because of their greater chemical and enzymatic stability, of having a longer action time when they are administered to a living organism.

Among the new peptides according to the invention, the peptides having cholecystokininergic properties are particularly useful.

Thus the present invention relates most particularly, but not exclusively, to new peptides having cholecystokininergic properties, their preparation and the therapeutic compositions which contain them.

It is known that at least two types of cholecystokininergic receptors exist, with different molecular weights [Sakamoto et al., J. Biol. Chem. 258, 12707 (1983); Sakamoto et al., Biochem. Biophys. Res. Comm., 124, 497 (1984)], which are capable of binding the following sulfated octapeptide (known as CCK$_8$):

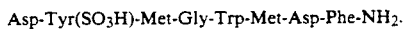

Asp-Tyr(SO$_3$H)-Met-Gly-Trp-Met-Asp-Phe-NH$_2$.

The receptors of the central nervous system are thus distinguished from the receptors of the peripheral nervous system. In the central nervous system, CCK$_8$ acts as a neurotransmitter [Golterman et al., J. Biol. Chem. 255, 6181 (1908)]. In addition, it is co-located with dopamine in certain neurons of the mesolimbic pathway [Hokfelt et al., Nature, 285, 476 (1980)]; it antagonizes its effects in the mesolimbic system and facilitates dopaminergic neurotransmission in the corpus striatum [Fuxe et al., Eur. J. Pharmacol., 67, 329 (1980)]. The peripheral receptors themselves are involved in the contraction of the smooth muscles of the intestine [Hutchinson et al., Eur. J. Pharmacol., 69, 87 (1981); Chang et al., Neuroscience Lett., 46, 71 (1984)] and in the liberation of pancreatic amylase [Jensen et al., J. Biol. Chem., 257, 5554 (1982)].

CCK$_8$, as well as other structurally related products, are known from German Patent Application 3,138,233 to have a neuropsychotropic action. In addition, this peptide has analgesic properties (Barbaz et al., Neuropharmacology, 25, 823 (1986)); it facilitates the processes of memorization (Katsuura and Itoh, Peptides, 87, 105 (1986)); it has anorexia-producing properties (Gibbs et al., J. Comp. Physiol. Psychol. 84, 488 (1973)), and it also accelerates intestinal motility (Mutt. Gastrointestinal hormones, Jersey Glass, G. B. Ed., Raven Press, New York, pages 169-221 (1980)).

Analogs of CCK$_8$ are known from the abovementioned German patent which have, in their peptide sequence, O-sulfated tyrosine as an amino acid, and which have only natural amino acids in their sequence. However, the practical significance of such products is limited because of the fact that the —O—SO$_3$H bond is easily hydrolyzable, as Bettelheim F. R. (J. Am. Chem. Soc., 76, 2838 (1954)) has reported. In the same way, these products are rapidly hydrolyzed at the peptide bonds by different classes of proteases (Durieux et al., Neuropeptides, 7, 1-9 (1986)).

It was therefore worthwhile to seek products analogous to CCK$_8$ but having a greater stability, while conserving or improving the properties of CCK$_8$. It is particularly important to observe that certain modifications in the sequence of the cholecystokininergic peptides, which are made according to the invention, lead to peptides which are closely related to, and selective for, the central CCK receptors (type B) as against the peripheral CCK receptors (type A), thus making them useable as specific therapeutic tools for the central nervous system.

The subject of the present invention is therefore, firstly, chemical compounds represented by the formula:

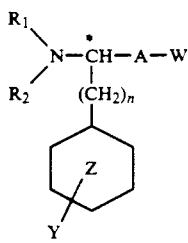

in which:
each of $R_1$ and $R_2$ each independently represents a hydrogen atom; a straight- or branched-chain $C_1$-$C_8$ alkyl radical, optionally substituted; a $C_3$-$C_7$ cycloalkyl radical or a mono- or polycyclic aromatic residue, optionally substituted;
in the case in which $R_1$ represents a hydrogen atom, $R_2$ being also capable of representing a radical which protects the amine function, of the acyl type or the urethane type, or even an amino acid residue or a peptide fragment;
$R_1$ and $R_2$ being also capable nitrogen atom to which they are attached, a 5- to 7-component ring capable of containing another heteroatom, and capable of being substituted by a straight- or branched-chain $C_1$-$C_8$ alkyl radical;
A represents carbonyl or methylene;
W represents hydroxy, phenoxy, $C_1$-$C_8$ alkoxy, phenoxy-($C_1$-$C_8$ alkyl), amino, optionally substituted ($C_1$-$C_8$ alkyl )-amino or di($C_1$-$C_8$ alkyl)-amino, the alkyl fractions of which can be substituted and/or can form, with the nitrogen atom to which they are attached, a 4-6 component ring capable of containing another heteroatom;
or when A represents carbonyl, W represents an amino acid residue
Y represents a residue chosen from those of formula:

$$—OSO_2OR_3 \quad (II);$$

$$—OPO(OR_3)_2 \quad (III);$$

$$—(CH_2)_m—SO_2OR_3 \quad (IV);$$

and $$—(CH_2)_m—PO(OR_3)_2 \quad (V),$$

where:
$R_3$ represents a hydrogen atom or a straight- or branched-chain $C_1$-$C_8$ alkyl radical, optionally substituted; and
m is from 1 to 4;
Z represents a 6-component ring chosen from the cyclohexane, pyridyl or phenyl rings, optionally substituted; and
n is from 0 to 4;
on the condition that, when Y represents a (III) or (IV) residue, it cannot be in meta position or it cannot be in ortho position if $R_3$ is a hydrogen atom,
and on the condition that when AW represents a carboxyl group, $R_1$, $R_2$ and $R_3$ representing some hydrogen atoms,
if Y represents (III) residue in para position, n is different from 0 and 1,
if Y represents (V) residue in para position, if n is equal to 0, m is different from 1 and 2, and if n is equal to 1, m is different from 1,
the said compounds being in the D, L or DL forms, as well as their mixtures and their pharmaceutically acceptable salts.

The alkyl radicals falling within the definitions of $R_1$ and $R_2$ can be substituted, for example by phenyl, which is itself optionally substituted, for example, by halogen. The aromatic residues falling within the definition of $R_1$ and $R_2$ are, for example, phenyl residues. The cycloalkyl or aromatic residues falling within the definition of $R_1$ and $R_2$, can be substituted, for example, by at least one halogen atom. When $R_1$ and $R_2$ together form a ring containing a heteroatom, the latter can be oxygen, sulfur or nitrogen.

The alkyl radicals falling within the definition of certain substituents indicated by W, are straight- or branched-chain radicals. The alkylamino and dialkylamino radicals falling within the definition of W can be substituted, for example, by phenyl. In the case in which W signifies dialkylamino and in which the alkyl fractions form a heterocycle containing a heteroatom, this latter can be oxygen, sulfur or nitrogen.

In the case in which the alkyl residue falling within the definition of $R_3$ is substituted, the substituent can be, among others, phenyl.

On the other hand, Z, which represents, in particular, phenyl, can be substituted on the ring, for example, by at least one substituent chosen from halogen, hydroxy, alkyl, alkoxy, hydroxyalkyl or alkoxyalkyl.

The radical of the acyl type which protects the amine function, and falls within the definition of $R_2$, is, for example, a formyl, acetyl, chloroacetyl, trifluoroacetyl, propionyl, butyryl, isobutyryl, $\gamma$-chlorobutyryl, oxalyl, succinyl, glutamyl, pyroglutamyl, phthalyl or p-toluenesulfonyl radical.

As for the radical of the urethane type which protects the amine function, and falls within the definition of $R_2$, it is, for example, a tert-butyloxycarbonyl, isopropyloxycarbonyl, ethoxycarbonyl, allyloxycarbonyl, benzyloxycarbonyl or mono- or polyhalobenzyloxycarbonyl radical.

Another subject of the invention is chemical compounds of formula (I) in which:
each of $R_1$ and $R_2$ each independently represents a hydrogen atom; a straight- or branched-chain $C_1$-$C_8$ alkyl radical, optionally substituted; a $C_3$-$C_7$ cycloalkyl radical or a mono- or polycyclic aromatic residue, optionally substituted;
in the case in which $R_1$ represents a hydrogen atom, $R_2$ being also capable of representing a radical which protects the amine function, of the acyl type or the urethane type, or even an amino acid residue or a peptide fragment;
$R_1$ and $R_2$ being also capable of forming, with the nitrogen atom to which they are attached, a 5- to 7-component ring capable of containing another heteroatom, and capable of being substituted by a straight- or branched-chain $C_1$-$C_8$ alkyl radical;

A represents —CO

Y represents a residue chosen from those of formula:

$-OSO_2OR_3$ (II);

$-OPO(OR_3)_2$ (III);

$-(CH_2)_m-SO_2OR_3$ (IV);

and $-(CH_2)_m-PO(OR_3)_2$ (V).

where:
$R_3$ represents a hydrogen atom or a straight- or branched-chain $C_1-C_8$ alkyl radical, optionally substituted; and m is from to 4;

Z represents a 6-component ring chosen from the cyclohexane, pyridyl or phenyl rings, optionally substituted; and n is from 0 to 4;

W represents:

-B-D-Trp-E-Asp-PheNHQ.

where:

B and E, which may be identical or different, represent a residue chosen from methionine, norleucine, leucine, serine, threonine, allothreonine, cysteine, homocysteine and the corresponding N-methylated derivatives, the OH or SH functions of serine, threonine, allothreonine, cysteine and homocysteine residues or their corresponding N-methylated derivatives being capable of being free or protected;

D represents a glycine residue;

Q represents hydrogen or a straight- or branched-chain $C_1-C_8$ alkyl group, optionally substituted, or even phenyl or phenylalkyl, the alkyl fraction of which has a straight or branched chain and contains 1 to 8 carbon atoms, the phenyl fraction of which can be substituted;

B being capable also of representing a 1,1-diaminoalkyl, 1,1-diaminomethylthioalkyl, 1,1-diaminomercaptoalkyl or 1,1-diaminohydroxyalkyl residue, the alkyl fractions being $C_1-C_8$, with a straight or branched chain, optionally substituted by a cycloalkyl residue or aromatic residue, and, in all cases, D necessarily representing a malonic residue.

on the condition that when Y represents a (II) or (III) residue, the sequence-AW is other than a sequence composed of natural amino acids, and when Y is in para position it does not represent a (II) residue, the said compounds being in the D, L or DL forms, as well as their mixtures and their pharmaceutically acceptable salts.

According to the definition of the invention, by "sequence of natural amino acids" is understood any of the combinations, in any order, of amino acids as described in Lehninger's work "Biochimie", page 67, Ed. Flammarion-Médecine-Science.

The OH or SH functions of the serine, threonine, allothreonine, cysteine or homocysteine residues or of their N-methylated derivatives, falling within the definition of B and E, can be protected, in particular, by:

i) an alkyl radical having 1 to 8 carbon atoms, with a straight or branched chain;

ii) a phenyl radical, unsubstituted or substituted by one or several fluorine atoms;

iii) a benzyl radical, unsubstituted by substituted by one or several fluorine atoms;

iv) an alkylcarbonyl radical, the alkyl part of which contains 1 to 5 carbon atoms, in a straight or branched chain, or a benzyl, phenacetyl or benzhydrylcarbonyl radical, the phenyl parts of which can be unsubstituted or substituted by one or several fluorine atoms.

The residues falling within the definition of B when D represents a malonic acid residue, are in particular 1,1-diaminopentane, 1,1-diamino-3-methylbutane, 2-hydroxy-1,1-diaminoethane, 2-hydroxy-1,1-diaminopropane, 1,1-diamino-3-methylthiopropane, 2-mercapto-1,1-diaminoethane or 3-mercapto-1,1-diaminopropane residues, the OH or SH functions of which are free or protected as indicated above for the cysteine or homocysteine residues.

The alkyl and phenyl residues falling within the definition of Q can be substituted by at least one fluorine atom.

The present invention also has as a subject processes for the preparation of compounds represented by the formula (I) as defined above.

In the case where Y represents a radical of formula (IV), also as defined above, this process is characterized by the fact that:

an alkaline sulfite (sodium sulfite) is reacted with a compound of general formula (VI):

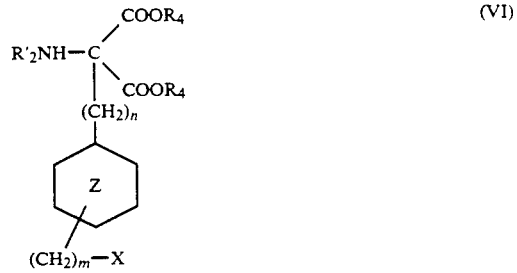

in which:

$R'_2$ represents a group which protects the amine function, as defined above for $R_2$, $R_4$ represents an alkyl radical;

X represents halogen, such as chlorine;

m, n and Z being as defined above;

then the intermediate product is hydrolyzed and decarboxylated to obtain a compound of general formula (Ia):

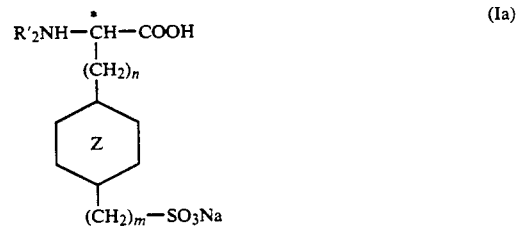

then the compound obtained is isolated and converted, if desired, to another compound of general formula (I), in which Y represents a radical of general formula (IV), by any method known per se, and the compound obtained is optionally converted to a pharmaceutically acceptable salt.

The action of sodium sulfite on the product of general formula (VI) generally takes place by heating to a temperature of between 100° and 120° C., in the presence of an aqueous inorganic base, such as caustic soda or caustic potash. The subsequent hydrolysis and decarboxylation are carried out by heating to a temperature of between 100° and 120° C., in the presence of a strong inorganic acid, such as aqueous hydrochloric acid.

The conversion of the product of general formula (Ia) to another product of general formula (I) can be carried out by any method known to those versed in the technique for converting, for example, a carboxylic or sulfonic acid to an ester, an ester to an alcohol, an ether or an amine, or for converting an amide to an amine, alkylating or acylating an amine or unblocking an amine function.

The products of formula (VI) can be obtained by the action of thionyl chloride on an alcohol of general formula (VII):

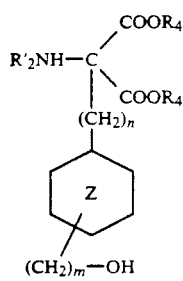

(VII)

in which the symbols are defined as above, operating without a solvent or in an organic solvent, such as methylene chloride, at the reflux temperature of the reaction mixture.

The products of general formula (VII) can be obtained by the action of sodium nitrite on a product of general formula (VIII):

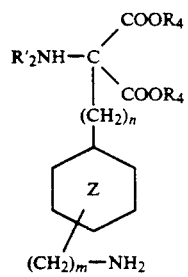

(VIII)

in which the symbols are defined as above, followed by hydrolysis of the diazo compound formed as an intermediate, in the normal conditions known to those versed in the technique.

The products of general formula (VIII) can be obtained by reduction of a product of general formula (IX):

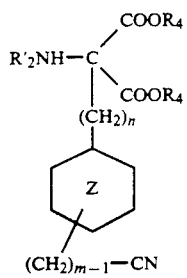

(IX)

in which the symbols are defined as above, operating by any known method, for example by reduction with hydrogen in the presence of a catalyst, such as palladium-on-charcoal, in an alcohol, such as methanol or ethanol.

The products of general formula (IX) can be prepared by the action of a product of general formula (X):

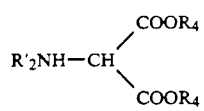

(X)

in which $R'_2$ and $R_4$ have the definitions given above, on a product of general formula (XI):

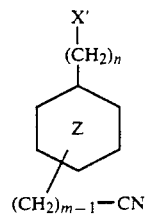

(XI)

in which X' represents a halogen atom, and the other symbols are defined as above, operating in the normal conditions, in the presence of an organic base, such as an alkaline ethylate.

The present invention also has as a subject a process for the preparation of a compound represented by formula (I) as defined above, in which Y represents a radical of general formula (V), also as defined above, this process being characterized in that:

a phosphite of general formula (XII):

P(OR'$_3$)$_3$     (XII)

where $R'_3$ represents an alkyl radical, as defined above for $R_3$, is reacted with a compound of general formula (VI):

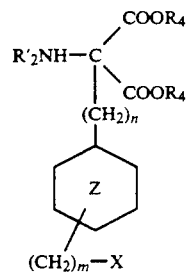

(VI)

in which:

R'$_2$ represents an alkyl radical as defined above for R$_2$;

R$_4$ represents an alkyl radical;

X represents halogen, such as chlorine;

m, n and Z being as defined above;

then the intermediate product is hydrolyzed and decarboxylated to obtain a compound of general formula (Ib):

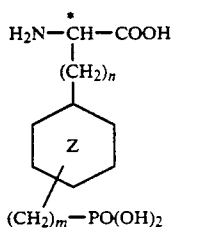

$$H_2N-CH-COOH \quad (Ib)$$
$$|$$
$$(CH_2)_n$$
$$(CH_2)_m-PO(OH)_2$$

then the product obtained is isolated, optionally in the form of a salt, and converted, if desired, to another product of general formula (I) in which Y represents a radical of general formula (V), by any method known per se, and the desired product is optionally converted to a pharmaceutically acceptable salt.

The action of the phosphite of general formula (XII) on the product of general formula (VI) is carried out by heating the reaction mixture under reflux.

The hydrolysis is carried out by any method known per se, for example, in an alkaline medium, by means of an inorganic base, such as caustic soda or caustic potash, at a temperature of between 20° C. and 80° C.

The decarboxylation of the product resulting from hydrolysis is carried out by heating in an acid medium, such as aqueous hydrochloric acid, at a temperature near the reflux temperature of the reaction mixture.

The conversion of the product of general formula (Ib) to another product of general formula (I) can be carried out by any method known to those versed in the technique for converting, for example, a carboxylic or phosphonic acid to an ester, an ester to an alcohol, an ether or an amine, or for converting an amide to an amine, alkylating or acylating an amine or for unblocking an amine function.

The products of general formula (I) in which
-A represents —CO—; and
-W represents: -B-D-Trp-E-Asp-Phe-NHQ B, D, E and Q being as defined above, can be prepared in the following manner:

a peptide of general formula (XIII):

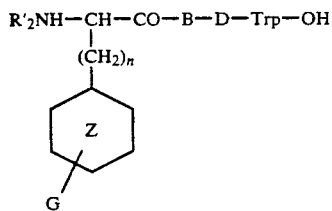

$$R'_2NH-CH-CO-B-D-Trp-OH \quad (XIII)$$
$$|$$
$$(CH_2)_n$$
Z
G or an activated derivative of that acid, where:

R'$_2$ represents an amine-protecting radical such as defined above for R$_2$;

G represents OH, or a radical of formulae (IV) or (V), as defined with respect to formula (I); and the other symbols are as defined above with respect to formula (I);

is coupled with the tripeptide of formula (XIV):

$$H\text{-}E\text{-}Asp\text{-}PheNH_2 \quad (XIV)$$

where E is as defined above, this tripeptide optionally being protected, then the protective group(s) are removed, and the product obtained is isolated in the free state or in the state of a salt, and it is optionally converted to another product as defined above, by any method known per se, and the final product is converted, if desired, to a pharmaceutically acceptable salt or a product in the free state, depending on the circumstances.

The products of general formula (XIII) and (XIV) are coupled by any method known to those versed in the technique for condensing a peptide with another peptide.

It is particularly advantageous to use the peptide of general formula (XIII) in an activated form. The product of the reaction of the compound of general formula (XIII) with hydroxybenzotriazole, N-hydroxysuccinimide, p-nitrophenol or tri- or pentachlorophenol, prepared in the presence of a condensation agent, may be mentioned as an activated form.

In practice, it is particularly advantageous to use, as an activated form, the product of the reaction with N-hydroxysuccinimide in an organic solvent, such as an ether, like tetrahydrofuran, a chlorinated solvent, like methylene chloride or chloroform, an amide, like dimethylformamide, or a mixture of these solvents, in the presence of dicyclohexylcarbodiimide, at a temperature of about 0° C.

The tripeptide of formula (XIV) can be obtained according to the method described by Ruiz-Gayo et al., Peptides, 6, 415 (1985).

The product of general formula (XIII) can be obtained by coupling the peptide of formula (XV):

$$H\text{-}B\text{-}D\text{-}Trp\text{-}OH \quad (XV)$$

where B and D are as defined above, with an amino acid of general formula (XVI):

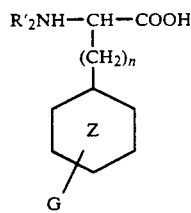

$$R'_2NH-CH-COOH \quad (XVI)$$
$$|$$
$$(CH_2)_n$$
Z
G in which:

G represents OH, or a radical of formulae (IV) or (V), as defined with respect to formula (I);

the symbols R'$_2$, n and Z are as defined above, with respect to formula (I).

Coupling is carried out by any method known per se, in peptide chemistry, in particular by the method, the conditions of which are indicated above, for coupling products of general formulae (XIII) and (XIV).

The product of general formula (XV) can be prepared according to the method described by Ruiz-Gayo et al., Peptides, 6, 415 (1985).

The products of general formula (I) in which the -A-W chain represents

—CO—B-D-Trp-E-Asp-Phe-NHQ (B, D, E and Q being as defined above) can also be prepared by coupling a peptide of general formula:

H-B-D-Trp-E-Asp(OR$_5$)-Phe-NH-Q  (XVII)

where:
B, D, E and Q are as defined above; and
R$_5$ represents a carboxylic acid-protecting radical, and, more particularly, a tert-butyl or benzyl group,
with a compound of formula (XVI), as defined above.

The coupling is carried out by any method known to those versed in the technique for condensing an amino acid with a peptide, in particular according to the processes indicated above.

The product of general formula (XVII) is obtained after deprotection of the terminal amine function of the hexapeptide:

R″$_2$-B-D-Trp-E-Asp-Phe—NHQ  (XVIII)

(where R″$_2$ is defined as for R$_2$ and R′$_2$), obtained by condensation of the dipeptide:

R″$_2$-B-D—OH  (XIX)

with the tetrapeptide of formula:

H-Trp-E-Asp(OR$_5$)-Phe—NHQ  (XX)

in which formulae R″$_2$, B, D, E, Q and R$_5$ are as defined above.

It is particularly advantageous to use this method of preparation in the case in which the B residue is a 1,1-diaminoalkyl, 1,1-diaminomethylthioalkyl, 1,1-diaminomercaptoalkyl or 1,1-diaminohydroxyalkyl residue, and the D residue is a malonic acid residue. In all these cases, the dipeptide R″$_2$-B-D—OH, therefore having a retro-inverso bond, is synthesized from an amino acid R″$_2$—F—OH, —F— being such that that amino acid shall be a precursor of the B residue, as it has been defined above, corresponding to the B residue in a Curtius transposition.

Synthesis of the retro-inverso dipeptide is carried out according to the general method described by Chorev and Goodman, Int. J. Peptide Protein Research, 21, 258 (1983). The amino acid R″$_2$—F—OH is activated on the carboxylic function in the form of an acyl azide, then, by heating, it is converted to the isocyanate derivative, on which the malonic acid is condensed to give the retro-inverso dipeptide R″$_2$-B-D—OH (XIX). It is particularly advantageous to protect the amine function with a benzyloxycarbonyl group.

The tetrapeptide of general formula (XX) is obtained according to a general method of peptide synthesis using a step-by-step process, starting with the compound H-Phe—NHQ, as has been described by Bodanszky et al., J. Med. Chem. 21, 1030 (1978).

In the case in which the Y group corresponds to general formula (II), the sulfuric hemiester function is obtained by sulfation of the phenol function of the tyrosine of a peptide of general formula (I), using the sulfur dioxide-pyridine complex.

In the case in which the Y group corresponds to general formula (III), the phosphoric ester function is obtained in particular with diethylchlorophosphonate according to the method of Valerio et al. (Tetrahedron Letters, Vol. 25, page 2609, 1984).

As those versed in the technique will readily notice, it is necessary, in order to implement the process according to the invention, to carry out reactions, at various stages of the synthesis, on products the acid or amine functions of which should already have been protected. In this case, the protecting radical will be removed at the most convenient time during synthesis, in particular before coupling the amino acids or the peptides together. In a nonlimiting manner, the functions could, for example, be protected in the following way:

For the amine functions, the protecting radicals listed for the definition of symbol R′$_2$ above could be used. When blocking is carried out on an intermediate product, and is therefore intended to be removed subsequently, it is advantageous to use the tert-butyloxycarbonyl radical; this could then be removed in relatively mild conditions, for example in an acid medium using trifluoroacetic acid undiluted, or diluted in methylene chloride, or using a solution of gaseous hydrochloric acid in an anhydrous solvent, such as dioxane or acetic acid; the peptide or the amino acid is then often isolated in the form of the trifluoroacetate or the acetate. The base could be liberated at the desired moment, using a stronger base such as triethylamine or N,N'-diisopropylethylamine.

For the acid functions, the ester radicals which are normally used in peptide chemistry and which are easily removable subsequently could be used, for example.

It is particularly advantageous to block the acid functions in the form of methyl or ethyl esters, which will then be removed by saponification using an aqueous solution of an alkaline hydroxide, such as caustic soda.

When, in addition to the C-terminal acid function, there exists another acid function carried on the side chain of an amino acid, such as aspartic acid, this acid function could advantageously be blocked with another type of radical, in order to subsequently unblock the acid functions selectively. In the case of aspartic acid, for example, a benzyloxy radical could be used, which could then be removed by hydrogenolysis in the presence of a catalyst, such as palladium on activated charcoal.

The diastereoisomeric forms of the peptides which result from the introduction into their sequence of the modified tyrosine residue, in which Y corresponds to formula (IV) or (V), can optionally be separated according to the normal methods, such as chromatography.

The new products of general formula (I), as well as the synthetic intermediates, can be purified, if necessary, by the normal methods, such as crystallization, chromatography or the formation of salts.

When the products of general formula (I) have, within their molecule, a free amine function, they can be converted to addition salts with acids by the action of an acid, working in an organic solvent, such as an alcohol, a ketone, an ether or a chlorinated solvent. The salt precipitates, optionally after concentration of its solution; it is separated by filtration or decantation.

The salts of inorganic acids, such as hydrochlorides, sulfates or phosphates, and the salts of organic acids, such as acetates, propionates, succinates, benzoates, fumarates, maleates, methanesulfonates, isethionates, theophyllineacetates, salicylates, phenolphthalinates, methylene-bis-β-oxynaphthoates or substitution derivatives of these compounds can be mentioned as addition salts with acids.

When the products of general formula (I) contain a salifiable acid function in their molecule, it is sometimes advantageous to isolate them in the form of a sodium or potassium salt. The free acids can then be, if desired, liberated from their salts according to the normal techniques, and can be, if desired, reconverted to another salt with a base.

Sodium or potassium salts or addition salts with nitrogenous bases, such as the salts of ethanolamine or lysine, can be mentioned as examples of salts with bases.

The new compounds according to the invention of general formula (I) have worthwhile pharmacological properties, which render them useful in the treatment of nervous diseases of central origin, in particular in the case where these compounds show a selectivity for receptors of the central type; the compounds of formula (I) also have an interest for their analgesic, anorexia-producing and intestinal motility stimulatory properties.

The amino acids and their derivatives have in fact been shown to be active in vitro in the test for affinity with excitatory amino acid receptors. These properties are demonstrated by the measurement of the inhibitory power ($K_i$) which the products exert on the binding of tritiated D-2-amino-5-phosphonopentanoic acid, which is abbreviated as [$^3$H]D-AP$_5$, to the cortical membranes of rats, according to the technique described by Olverman et al., Nature 307, 460–462 (1984) and Eur. J. Pharmacol., 131. 161–162 (1986).

The products according to the invention have a low toxicity. Their LD$_{50}$ is generally between 50 and 100 mg/kg by the intravenous route, and between 100 and 150 mg/kg by the subcutaneous route, in the mouse.

The peptides according to the invention have also been shown to be active in vitro in tests for affinity with receptors of the central nervous system and the peripheral nervous system (pancreas, smooth intestinal muscles). These properties are demonstrated, on the one hand, in binding tests on mouse brain membranes, and, on the other hand, in pharmacological tests for the liberation of guinea pig pancreatic amylase and for the contraction of guinea pig ileum.

The present invention also relates to medicaments constituted of a product of general formula (I), in the free form or in the form of an addition salt with a pharmaceutically acceptable acid or base, in the pure state or in the form of a composition in which it is associated with any other pharmaceutically compatible product, which may be inert or physiologically active. The medicaments according to the invention can be used by the oral, parenteral or rectal routes, or in the form of patches.

Tablets, pills, powders (in particular in gelatin capsules or cachets) or granules may be used as solid compositions for oral administration. In these compositions the active product according to the invention is mixed with one or several inert diluents, such as starch, cellulose, sucrose, lactose or silica. These compositions can also contain substances other than diluents, for example one or several lubricants, such as magnesium stearate or talc, a colorant, a coating (sugar-coated pills) or a varnish.

Pharmaceutically acceptable solutions, suspensions, emulsions, syrups and elixirs containing inert diluents such as water, ethanol, glycerol, vegetable oils or paraffin oil, may be used as liquid compositions for oral administration. These compositions can also contain substances other than diluents, for example wetting agents, sweeteners, thickeners, flavorings or stabilizers.

Sterile compositions for parenteral administration can preferably be aqueous or non-aqueous solutions, suspensions or emulsions. Water, propylene glycol, a polyethylene glycol, vegetable oils, in particular olive oil, injectable organic esters, for example ethyl oleate, or other suitable organic solvents can be used as solvent or vehicle. These compositions can also contain adjuvants, in particular wetting agents, isotonizers, emulsifiers, dispersants and stabilizers. Sterilization may be carried out in several manners, for example by aseptic filtration, by incorporating sterilizing agents in the composition, by irradiation or by heating. Sterile compositions for parenteral administration can also be prepared in the form of solid sterile compositions which can be dissolved at the time of use in a sterile injectable medium.

Compositions for rectal administration are suppositories or rectal capsules, which contain, in addition to the active product, excipients such as cocoa butter, semi-synthetic glycerides or polyethylene glycols.

In human therapeutics, amino acids and their derivatives, as well as the peptides according to the invention, are particularly useful in the treatment and prevention of diseases related to the neuronal destruction produced by anoxic ischemias, the damage caused to the cerebral tissue by hypoglycemic attacks in particular in the elderly adult, epileptic fits, and more generally the degenerative diseases which are linked with ageing (Alzheimer's disease) or are genetic (Huntington's chorea) as well as for their facilitating action on the memorization processes; the peptides according to the invention are particularly useful in the treatment of diseases of the central nervous system in which a dys-function of the dopaminergic pathways occurs, for example in Parkinson's disease, the choreas, schizophrenia, the late dyskinesias or manic-depressive episodes.

Thus, the compounds of formula (I) have antipsychotic properties, making them useful as neuroleptic agents; a facilitating effect on the processes of memorization, making them useful in elderly subjects for palliation of the ageing of nerve cells; analgesic properties; they are useful as anorexia-producing agents, and they have stimulating effects on intestinal motility, making them useful for reducing intestinal transit time.

The doses depend on the effect required and on the duration of treatment; they are generally between 2 and 100 mg per day by the parenteral route for an adult, in one or several doses.

In a general manner, the doctor will determine the most appropriate dosage in view of the age, the weight and all the other factors pertaining to the subject to be treated.

In order better to illustrate the subject of the invention, several examples of its implementation will now be described.

EXAMPLE 1: MONOSODIUM N-ACETYL-4-SULFONATOMETHYL-PHENYLALANINE

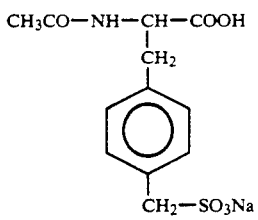

Stage 1: Preparation of ethyl 2-acetamido-2-(4-cyanobenzyl)malonate

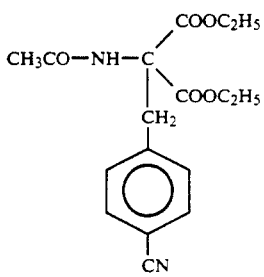

0.26 g of sodium is added to 25 cm³ of anhydrous ethanol. When all the sodium has disappeared, 2.17 g of ethyl acetamido malonate is added to the solution and the mixture is heated for 15 minutes to a temperature of about 110° C. 1.96 g of α-bromo-p-toluonitrile are added to the slightly cloudy solution obtained over 15 minutes, and the reaction mixture is heated for 17 hours to a temperature of about 110° C. After cooling, 50 cm³ of distilled water are added while maintaining stirring. The precipitate which forms is separated by filtration and washed with two times 10 cm³ of distilled water, then dried under reduced pressure (1 mm of mercury; 0.13 kPa) at 40° C. 2.89 g of ethyl 2-acetamido-2-(4-cyanobenzyl)malonate are thus obtained in the form of white crystals.

Rf: 0.73 [thin layer chromatography on silica gel; solvent: chloroform-methanol (90-10 by volume)].

Stage 2: Preparation of ethyl 2-acetamido-2-(4-aminomethylbenzyl)malonate hydrochloride

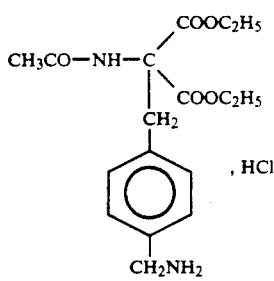

A current of hydrogen is bubbled into a suspension of 200 mg of palladium-on-charcoal catalyst in 4 cm³ of ethanol for 1 hour, until saturation, then a solution of 996 mg of ethyl 2-acetamido-2-(4-cyanobenzyl)malonate in 20 cm³ of ethanol is added, followed by 1.5 cm³ of an aqueous solution of concentrated hydrochloric acid.

The mixture is hydrogenated under atmospheric pressure, at a temperature of about 20° C. for 22 hours. The reaction mixture is then filtered and the catalyst is washed with 2 times 8 cm³ of ethanol. The filtrate and the washing liquors are pooled and concentrated to dryness under reduced pressure (20 mm of mercury; 2.7 kPa) at 30° C. The residue is taken up in 60 cm³ of distilled water and the solution obtained is stirred for 30 minutes. An insoluble residue is separated by filtration and the filtrate is concentrated to dryness under reduced pressure (1 mm of mercury; 0.13 kPa) at 40° C. 956 mg of ethyl 2-acetamido-2-(4-aminomethylbenzyl)-malonate hydrochloride are thus obtained in the form of a white solid.

Rf: 0.28 [thin layer chromatography on silica gel; solvent: chloroform-methanol-water-acetic acid-ethyl acetate (respectively 35-15-3-1.5-1 by volume)].

Stage 3: Preparation of ethyl 2-acetamido-2-(4-hydroxymethylbenzyl)malonate

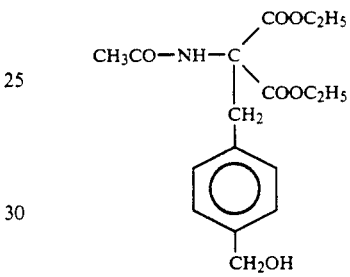

534 mg of sodium nitrite are added to a solution of 2.06 g of ethyl 2-acetamido-2(4-aminomethylbenzyl)malonate hydrochloride in 100 cm³ of distilled water, and the reaction mixture is heated for 2 hours at 110° C. After cooling, the mixture is extracted with 2 times 150 cm³ of ethyl acetate. The organic phases are pooled and washed successively with 100 cm³ of a 1N aqueous solution of hydrochloric acid, then with 100 cm³ of a 5% aqueous solution of sodium bicarbonate, and finally with 100 cm³ of a saturated aqueous solution of sodium chloride, then dried over sodium sulfate; the solution is filtered and the filtrate is evaporated to dryness under reduced pressure [20 mm of mercury (2.7 kPa), then 1 mm of mercury (0.13 kPa)] at 40° C. 1.67 g of ethyl 2-acetamido-2-(4-hydroxymethylbenzyl)malonate are thus obtained in the form of a white solid.

Rf=0.15 [thin layer chromatography on silica gel; solvent: hexane-ethyl acetate-methanol (60-40-4 by volume)].

Stage 4: Preparation of ethyl 2-acetamido-2-(4-chloromethylbenzyl)malonate

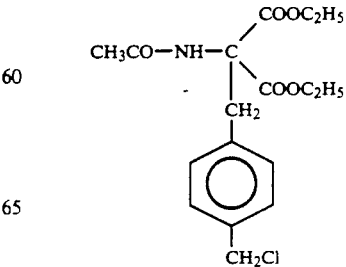

1.4 cm³ of thionyl chloride are added to a solution of 210 mg of ethyl 2-acetamido-2-(4-hydroxymethylbenzyl)malonate in 15 cm³ of dichloromethane, and the reaction mixture is heated under reflux for 23 hours. The dichloromethane and the excess thionyl chloride are removed by evaporation under reduced pressure [20 mm of mercury (2.7 kPa), then 1 mm of mercury (0.13 kPa)] at 40° C. The residue is washed with 2 times 3 cm³ of ethyl ether and dried under reduced pressure (20 mm of mercury; 2.7 kPa). 161 mg of ethyl 2-acetamido-2-(4-chloromethylbenzyl)malonate are thus obtained in the form of a white solid.

Rf=0.62 [thin layer chromatography on silica gel; solvent: dichloromethane-methanol (80-5 by volume)].

Stage 5: Preparation of the Desired Product 1.1 g of ethyl 2-acetamido-2-(4-chloromethylbenzyl)malonate are added to a solution of 3.31 g of sodium sulfite in 20 cm³ of distilled water, and 8 cm³ of a 10% aqueous solution of caustic soda, and the reaction mixture is heated for 3 hours to a temperature of about 120° C. After cooling to a temperature of about 20° C., the reaction mixture is taken to pH=1 by means of a 1N aqueous solution of hydrochloric acid, and the mixture is again heated to 120° C. for 1 hour. The reaction mixture is cooled to a temperature of about 20° C., and taken up in 150 cm³ of ethanol; the inorganic salts are separated off by filtration and the filtrate is concentrated to dryness under reduced pressure (20 mm of mercury; 2.7 kPa) at 30° C. The residue obtained is passed through a 2.5 cm diameter chromatography column packed with 100 g of silica gel, eluting with a mixture of dichloromethane, methanol, water and acetic acid (respectively 70-30-6-3 by volume). 424 mg of monosodium N-acetyl-4-sulfonatomethylphenylalanine are thus obtained.

Proton NMR spectrum (270 MHz; D₂O): 1.53 ppm, s: 3H (C$\underline{H}_3$—CO—), 2.55 ppm and 2.81 ppm, dd: 2H

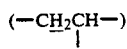

3.77 ppm, s: 2H (—C$\underline{H}_2$—SO₃Na), 4.11 ppm, m: 1H

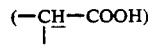

6.88 ppm, d: 2H and 6.97 ppm duplet: 2H (H aromatics).

Mass spectrum using FAB ionization: m/e=324 (MH+) (theoretical: 324).

Rf=0.16 [thin layer chromatography on silica gel; solvent: dichloromethane-methanol-water-acetic acid (70-30-6-3 by volume)].

EXAMPLE 2: 4-PHOSPHONOMETHYLPHENYLALANINE HYDROCHLORIDE

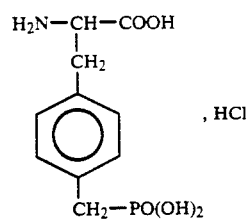

Stage 1: Preparation of tetraethyl 2-acetamido-2-(4-phosphonatomethylbenzyl)malonate

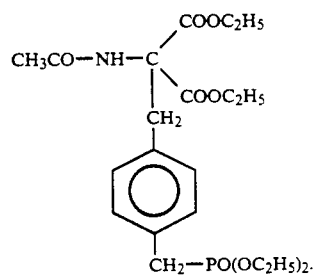

A mixture of 50 mg of ethyl 2-acetamido-2(4-chloromethylbenzyl)malonate and 4 cm³ of ethyl phosphite is heated under reflux for 17 hours. The excess ethyl phosphite is evaporated under reduced pressure (1 mm of mercury; 0.13 kPa) at 40° C. An oil is obtained, which is purified by "flash" chromatography on a 1 cm diameter column, packed with 8 g of silica (230–400 mesh - 40-63 μm), eluting with a mixture of dichloromethane and methanol (90-10 by volume). 42.6 mg of tetraethyl 2-acetamido-2-(4-phosphonatomethylbenzyl)malonate are obtained in the form of a white solid.

Rf=0.17 [thin layer chromatography on silica gel; solvent: dichloromethane-methanol (90-10 by volume)].

Stage 2: Preparation of the Desired Product 0.24 cm³ of a 1N aqueous solution of caustic soda is added to a solution of 27.5 mg of tetraethyl 2-acetamido-2-(4-phosphonatomethylbenzyl)malonate thus prepared in 1 cm³ of distilled water and 1 cm³ of methanol, and the mixture is stirred for 3 hours at a temperature of about 20° C. 4 cm³ of distilled water and 2.5 cm³ of a concentrated aqueous solution of hydrochloric acid are then added, and the mixture is heated under reflux for 4 hours. After cooling to a temperature of about 20° C., 10 cm³ of distilled water are added, and the pH is adjusted to 4 by means of a 10% aqueous solution of caustic soda. After lyophilization of the solution, and purification by chromatography on a column (φ 0.9 cm) with, as eluant, a mixture of 2-propanol and 28% NH₄OH (respectively 60–40 by volume), 9.5 mg of 4-phosphonomethylphenylalanine hydrochloride are obtained in the form of a white product.

Rf=0.10 [thin layer chromatography on silica gel; solvent: 2-propanol—28% NH₄OH (60–40 by volume)].

Proton NMR spectrum (270 MHz; D₂O) (TMS as external reference): 2.72 ppm and 2.80 ppm: s, 2H (—C$\underline{H}_2$—PO₃—), 2.84 ppm and 3.08 ppm: dd, 2H

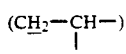

3.74 ppm: m, 1H

7.0 ppm and 7.10 ppm: d, 4H (H aromatics).

Working as described in Examples 1 and 2, and by subsequent operations on the products thus isolated, the following products were prepared:

EXAMPLE 3: MONOSODIUM N-ACETYL(4-SULFONATOMETHYL-2-METHOXY)PHENYLALANINE

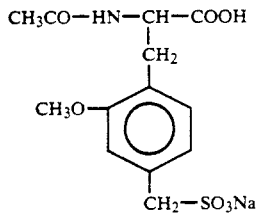

Rf=0.24 [thin layer chromatography on silica gel; solvent: dichloromethane-methanol-water-acetic acid (70-30-10-10 by volume)].

EXAMPLE 4: MONOSODIUM N-ACETYL(4-SULFONATOMETHYL)CYCLOHEXYLALANINE

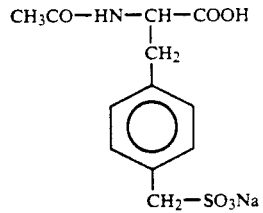

Rf=0.27 [thin layer chromatography on silica gel; solvent: dichloromethane-methanol-water-acetic acid (70-30-10-10 by volume)].

EXAMPLE 5: MONOSODIUM N-TETRAMETHYLENE(4-SULFONATOMETHYL)PHENYLALANINE

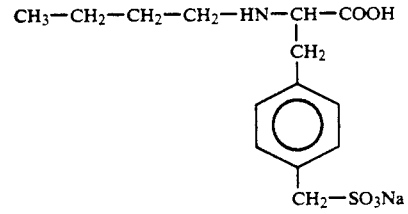

Rf=0.27 [thin layer chromatography on silica gel; solvent: dichloromethane-methanol-water-acetic acid (70-30-10-10 by volume)].

EXAMPLE 6: 2-AMINO-3-[4-(SULFONATOMETHYL)-PHENYL]PROPANOL

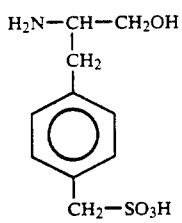

Rf=0.32 [thin layer chromatography on silica gel; solvent: dichloromethane-methanol-water-acetic acid (70-30-10-10 by volume)].

EXAMPLE 7: MONOSODIUM 4-(SULFONATOMETHYL)PHENYLGLYCINE HYDROCHLORIDE

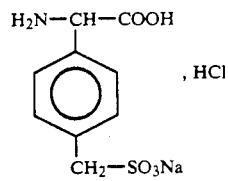

Rf=0.25 [thin layer chromatography on silica gel; solvent: dichloromethane-methanol-water-acetic acid (70-30-10-10 by volume)].

EXAMPLE 8: N-ACETYL-3-(PHOSPHONOMETHYL)-PHENYLALANINE

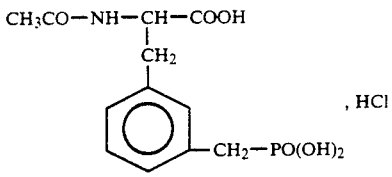

Rf=0.23 [thin layer chromatography on silica gel; solvent: dichloromethane-methanol-water-acetic acid (70-30-10-10 by volume)].

EXAMPLE 9: METHYL N-ACETYL-4-METHOXYSULFONYLMETHYL-PHENYLALANINATE

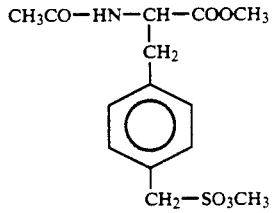

Rf=0.56 [thin layer chromatography on silica gel; solvent: dichloromethane-methanol-water-acetic acid (70-30-6-3 by volume)].

EXAMPLE 10:
4-(PHOSPHONOETHYL)PHENYLALANINE HYDROCHLORIDE

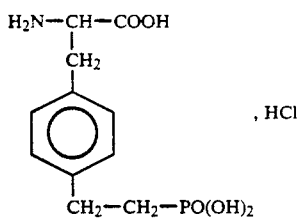

Rf=0.19 [thin layer chromatography on silica gel; solvent: dichloromethane-methanol-water-acetic acid (70-30-10-10 by volume)].

EXAMPLE 11:
N-ACETYL(4-DIETHYLOPHOS- PHONATOMETHYL-2,6-DICHLORO)- PHENYLALANINE

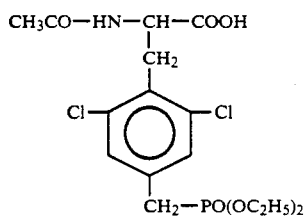

Rf=0.35 [thin layer chromatography on silica gel; solvent: dichloromethane-methanol-water-acetic acid (70-30-6-3 by volume)].

EXAMPLE 12:
2-AMINO-3-(4-PHOSPHONOMETHYLPHENYL)- N-BENZYLPROPANAMIDE

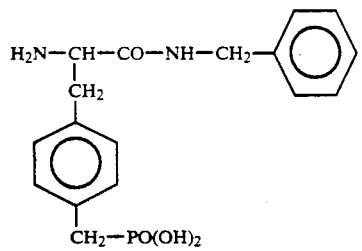

Rf=0.24 [thin layer chromatography on silica gel; solvent: dichloromethane-methanol-water-acetic acid (70-30-10-10 by volume)].

In the following examples, the amino acids are represented by the conventional abbreviated forms. The other abbreviations have the following meanings:

BOC = tert-butyloxycarbonyl
OBZ = benzyloxy
Ac = acetyl
DCC = dicyclohexylcarbodiimide
HOBt = 1-hydroxybenzotriazole
TFA = trifluoroacetic acid
gNle = gem-1,1-diaminopentane
mGly = malonic acid
HONSu = N-hydroxysuccinimide
Cbz = benzyloxycarbonyl

EXAMPLE 13:
Ac-L-Phe(p-CH$_2$SO$_3$)-NLe-Gly-Trp-NLe-Asp- PheNH$_2$ and

EXAMPLE 14:
Ac-D-Phe(p-CH$_2$SO$_3$Na)-NLe-Gly-Trp-NLe-Asp- PheNH$_2$

Stage 1: Preparation of
Ac-LD-Phe(P-CH$_2$SO$_3$Na)-NLe-Gly-Trp-OC$_2$H$_5$ 105 mg of H-NLe-Gly-Trp-OC$_2$H$_5$, 41.3 mg of 1-hydroxybenzotriazole and 55.6 mg of dicyclohexylcarbodiimide are successively added to a solution of 84.2 mg of monosodium N-acetyl-4-sulfonatomethyl-(LD)-phenylalanine (prepared as described in Example 1) in 6 cm$^3$ of dimethylformamide cooled to 0° C. The reaction mixture is stirred for 1 hour at 0° C., and for one night at a temperature of about 20° C. After evaporation of the dimethylformamide under reduced pressure (1 mm of mercury; 0.13 kPa), 10 cm$^3$ of ethyl acetate are added. The product and dicyclohexylurea precipitate. After removal of the supernatant, the product is dissolved in 40 cm$^3$ of water, while the dicyclohexylurea remains insoluble in the aqueous medium. After filtration, the aqueous phase is lyophilized. 147 mg of Ac-LD-Phe(p-CH$_2$SO$_3$Na)-NLe-Gly-Trp-OC$_2$H$_5$ are thus obtained in the form of a white product.

Rf=0.25 [thin layer chromatography on silica gel; eluant: dichloromethane-methanol-water-acetic acid (70-30-6-3 by volume)].

Stage 2: Preparation of
Ac-LD-Phe(p-CH$_2$SO$_3$Na)-NLe-Gly-Trp-OH 100 mg of the product obtained in stage 1 are dissolved in 8 cm$^3$ of water and 1 cm$^3$ of methanol, and the solution is cooled to 0° C. 0.3 cm$^3$ of a 1N aqueous solution of caustic soda is added to this solution. The reaction mixture is stirred for 1 hour at 0° C., and for 3 and a half hours at a temperature of about 20° C. After evaporation of the methanol, 5 cm$^3$ of water are added and the unsaponified product is removed by extraction with 6 cm$^3$ of ethyl acetate. The aqueous phase is acidified at 0° C. to pH=2 with a 1N aqueous solution of hydrochloric acid. After lyophilization, 90 mg of Ac-LD-Phe(p-CH$_2$SO$_3$Na)-Nle-Gly-Trp-OH are obtained in the form of a white product.

Rf=0.10 [thin layer chromatography on silica gel; solvent: dichloromethane-methanol-water-acetic acid (70-30-6-3 by volume)].

The absence of racemization of the tryptophane residue, at this stage in the synthesis, is monitored by $^1$H NMR (270 MHz).

Stage 3: Preparation of:
Ac-LD-Phe(p-CH$_2$SO$_3$Na)-NLe-Gly-Trp-NLe- Asp(OBZ)-PheNH$_2$ 5 μl of triethylamine, 20 mg of Ac-LD-Phe(p-CH$_2$SO$_3$Na)-NLe-Gly-Trp-OH (prepared as described in stage 2), 9.2 mg of 1-hydroxybenzotriazole and 12.4 mg of dicyclohexylcarbodiimide are successively added to a solution of 17.5 mg of H-NLe-Asp(OBZ)-Phe-NH$_2$,TFA in 2 cm$^3$ of dimethylformamide cooled to 0° C. The reaction mixture is stirred for 1 hour at 0° C., and for one night at a temperature of about 20° C. After evaporating the dimethylformamide under reduced pressure (1 mm of mercury; 0.13 kPa), 10 cm$^3$ of ethyl acetate and then 25 cm³ of ethyl ether are added. After stirring, settling and removal of the supernatant, the product is again washed with 20 cm³ of ether. After removal of the supernatant, the product is dried. 26.4 mg of Ac-LD-Phe(p-CH₂SO₃Na)-NLe-Gly-Trp-NLe-Asp(OBZ)-PheNH₂ are thus obtained in the form of a white product.

Rf=0.38 for the first diastereoisomer.

Rf=0.43 for the second diastereoisomer [thin layer chromatography on silica gel; solvent: dichloromethane-methanol-water-acetic acid-ethyl acetate (35-15-3-1.5-1 by volume)].

Stage 4: Preparation of the Racemic Mixture of the Products Desired

The product obtained in stage 3 is added to 14.7 mg of the same product coming from another operation, and the whole [that is 41.1 mg of Ac-LD-Phe(p-CH₂SO₃-Na)-NLe-Gly-Trp-NLe-Asp(OBZ)-PheNH₂] is dissolved in 8 cm³ of methanol. The solution is added to a suspension of 12 mg of catalyst containing 10% of palladium-on-charcoal in 2 cm³ of methanol, previously saturated with hydrogen for 1 hour and a half. Hydrogenolysis is continued for 2 hours at a temperature of about 20° C., under atmospheric pressure. After filtration and rinsing of the catalyst (twice with 6 cm³ of methanol), the solution is concentrated under reduced pressure (20 mm of mercury; 2.7 kPa) at 30° C. 30.7 mg of Ac-LD-Phe(p-CH₂SO₃Na)-NLe-Gly-Trp-NLe-Asp-PheNH₂ are thus obtained in the form of a white product.

Rf=0.23 for the first diastereoisomer.

Rf=0.20 for the second diastereoisomer [thin layer chromatography on silica gel; solvent: dichloromethane-methanol-water-acetic acid-ethyl acetate (35-15-3-1.5-1 by volume)].

Stage 5: Separation of the Diastereoisomers

Separation of the diastereoisomers is carried out on 21 mg of the mixture, by chromatography on a 0.9 cm diameter column, packed with 15 g of silica, eluting with a mixture of ethyl acetate, pyridine, acetic acid and water in the following respective proportions: 60-20-6-11 (by volume), collecting the eluate in tubes, each containing 50 drops.

5.1 mg of Ac-L-Phe(p-CH₂SO₃Na)-NLe-Gly-Trp-NLe-Asp-PheNH₂ (Example 13) are thus obtained.

Rf=0.26 [thin layer chromatography on silica gel; eluant: ethyl acetate-pyridine-acetic acid-water (60-20-6-11 by volume)].

HPLC: retention time=9 minutes; eluant: mixture of triethylamine phosphate buffer (0.025 M; pH=6.5) and acetonitrile (71-29 by volume); flow rate=1.2 cm³/minute.

Mass spectrum using FAB ionization: m/e=1054 (MH+).

3.6 mg of Ac-D-Phe(p-CH₂SO₃Na)-NLe-Gly-Trp-NLe-Asp-PheNH₂ (Example 14).

Rf=0.21 [thin layer chromatography on silica gel; eluant: ethyl acetate-pyridine-acetic acid-water (60-20-6-11 by volume)].

HPLC: retention time=7.8 minutes; eluant: mixture of triethylamine phosphate buffer (0.025 M; pH=6.5) and acetonitrile (71-29 by volume); flow rate=1.2 cm³/minute.

Mass spectrum using FAB ionization: m/e=1054 (MH+).

EXAMPLE 15:
Boc-Tyr(SO₃Na)-gNle-mGly-Trp-(N-Me)Nle-Asp(Na)-Phe-NH₂

Stage 1: Preparation of Boc-(N-Me)Nle-OH 0.125 g of 1,4,7,10,13,16-hexaoxacyclooctadecane and 0.77 ml of methyl iodide are successively added to a solution of 2.31 g of Boc-Nle-OH in 20 ml of tetrahydrofuran and 2.5 ml of dimethylformamide cooled to 0° C. The reaction mixture is stirred, under nitrogen, for 24 hours at ambient temperature, then it is acidified with 0.75M citric acid to pH 3. The aqueous phase is extracted with ether, then rinsed with a saturated aqueous solution of sodium chloride to neutrality. The organic phase is dried over sodium sulfate, filtered and evaporated to dryness under reduced pressure (20 mm of mercury; 2.7 kPa); at a temperature of about 40° C., to give 2.32 g of Boc-(N-Me)Nle-OH, in the form of an oil.

Rf=0.54 [silica gel; CHCl₃-MeOH (85-15 by volume)].

Stage 2: Preparation of Boc(N-Me)Nle-Asp(OBzl)-Phe-NH₂

0.84 ml of triethylamine, 1.47 g of Boc(N-Me)Nle-OH, 1.48 g of dicyclohexylcarbodiimide and 0.69 g of hydroxysuccinimide are successively added to a solution, cooled to 0° C., of 2.89 g of H-Asp(OBzl)-Phe-NH₂, prepared according to the method described by Charpentier et al. in "J. Med. Chem., 30, 962, 1987", in 15 cm³ of dimethylformamide and 15 cm³ of dichloromethane. The reaction mixture is stirred for 1 hour at 0° C., then for one night at a temperature of about 20° C. The solid formed is removed by filtration, and the filtrate is concentrated to dryness under reduced pressure (20 mm of mercury; 2.7 kPa), at a temperature of about 40° C. The oily residue is triturated with diethyl ether and ethyl acetate, then the solid is isolated by filtration. 3.14 g of Boc-(N-Me)-Nle-Asp(OBzl)-Phe-NH₂ are collected, in the form of a white solid melting at 55°-57° C.

Stage 3: Preparation of H-(N-Me)Nle-Asp(OBzl)-Phe-NH₂,TFA 3 g of Boc-(N-Me)Nle-Asp(OBzl)-Phe-NH₂ are dissolved in a mixture, cooled to 0° C., of 8 cm³ of methylene chloride and 8 cm³ of trifluoroacetic acid, and the reaction mixture is stirred for 45 minutes at 0° C. and 45 minutes at a temperature of about 20° C. The mixture is concentrated to dryness under reduced pressure (20 mm of mercury; 2.7 kPa) at 40° C. 2.67 g of H-(N-Me)Nle-Asp(OBzl)-Phe-NH₂,TFA are thus obtained.

Rf=0.22 [silica gel; chloroform-methanol (9-1 by volume)].

Stage 4: Preparation of Boc-Trp-(N-Me)Nle-Asp(OBzl)-Phe-NH₂

2.14 g of Boc-Trp-ONp and 0.64 g of HOBt are added to a solution, cooled to 0° C., of 2.5 g of H-(N-Me)Nle-Asp(OBzl)-Phe-NH₂,TFA in 20 cm³ of dimethylformamide containing 0.72 ml of diisopropylethylamine, and the reaction mixture is stirred under a nitrogen atmosphere for 30 minutes at 0° C., then for one night at a temperature of about 20° C. After evaporation of the solvent under reduced pressure (1 mm of mercury; 0.13 kPa) at 40° C., the oily residue obtained is purified by flash chromatography on silica gel, eluting with a mixture of chloroform and methanol (98-2 by volume). 2.54 g of Boc-Trp-(N-Me)Nle-Asp(OBzl)-Phe-NH₂ are thus obtained in the form of a white solid melting at 98°-100° C.

Rf=0.43 [silica gel; chloroform-methanol (9-1 by volume)].

Stage 5: Preparation of H-Trp-(N-Me)Nle-Asp(OBZ)-Phe-NH$_2$.TFA 3.18 g of Boc-Trp-(N-Me)Nle-Asp(OBZ)-Phe-NH$_2$ are dissolved in a mixture, cooled to 0° C., of 7 cm$^3$ of methylene chloride, 7 cm$^3$ of trifluoroacetic acid and 0.5 cm$^3$ of anisole, and the reaction mixture is stirred under nitrogen for 45 minutes at 0° C., and for 45 minutes at a temperature of about 20° C. The solvents are then evaporated under reduced pressure (1 mm of mercury; 0.13 kPa) at a temperature of about 40° C., and the residue obtained is precipitated with diethyl ether. 2.70 g of H-Trp-(N-Me)Nle-Asp(OBZ)-Phe-NH$_2$,TFA are thus obtained.

Rf=0.20 [silica gel; chloroform-methanol (9-1 by volume)].

Stage 6: Preparation of N-benzyloxycarbonyl-N'-malonyl-1,1-diaminopentane (Cbz-gNle-mGly-OH)

1.03 cm$^3$ of ethyl chloroformate are added to a solution, cooled to −20° C., of 2.65 g of Cbz-Nle-OH in 25 cm$^3$ of tetrahydrofuran containing 1.37 cm$^3$ of N-ethylmorpholine. The reaction mixture is stirred for 15 minutes at −15° C., and 1.3 g of sodium azide, in solution in 10 cm$^3$ of water, is added, and stirring is maintained for 30 minutes at 0° C. The reaction mixture is extracted with ethyl acetate at 0° C., and the organic phase is washed successively with a saturated aqueous solution of sodium chloride, a saturated aqueous solution of sodium bicarbonate, then again with a saturated aqueous solution of sodium chloride. The organic phase is dried over magnesium sulfate, then filtered and evaporated under reduced pressure (20 mm of mercury; 2.7 kPa) at 20° C. The oily residue is taken up in 40 cm$^3$ of toluene, and is heated to 80° C. for 10 minutes, then treated with a solution of 3.12 g of malonic acid in 15 cm$^3$ of dioxane. The reaction mixture is then heated to 80° C. for 30 minutes, then maintained at 0° C. for 1 day. The precipitate is washed with dichloromethane and purified by flash chromatography on silica gel, eluting with a mixture of chloroform, methanol and acetic acid (90-5-5 by volume), to give 1.6 g of Boc-gNle-mGly-OH, in the form of a white solid melting at 142°-145° C.

Rf=0.41 [silica gel; chloroform-methanol-acetic acid (90-5-5 by volume)].

Stage 7: Preparation of: Cbz-gNle-mGly-Trp-(N-Me)Nle-Asp(OBZ)-Phe-NH$_2$ 0.066 cm$^3$ of triethylamine, 0.18 g of Cbz-gNle-mGly-OH, 0.066 g of hydroxysuccinimide and 0.143 g of dicyclohexylcarbodiimide are successively added to a solution, cooled to 0° C., of 0.46 g of H-Trp-(N-Me)Nle-Asp(OBZ)-Phe-NH$_2$ in 3 ml of dimethylformamide. The reaction mixture is stirred under nitrogen for 1 hour at 0° C., then for one night at ambient temperature. The insoluble residue formed is removed by filtration, and the filtrate is condensed to dryness under reduced pressure (1 mm of mercury; 0.13 kPa). The oily residue obtained is precipitated with a mixture of diethyl ether and ethyl acetate. After purification of the precipitate by flash chromatography on silica gel, eluting with a chloroform-methanol mixture (97-3 by volume), 0.34 g of Cbz-gNle-mGly-Trp-(N-Me)Nle-Asp(OBZ)-Phe-NH$_2$ are thus obtained, in the form of a white solid melting at 190°-193° C.

Rf=0.39 [silica gel; chloroform-methanol (9-1 by volume)].

Stage 8: Preparation of: H-gNle-mGly-Trp-(N-Me)Nle-Asp-Phe-NH$_2$ 30 mg of palladium-on-activated-charcoal (10% by weight) are added to a solution of 0.32 g of Cbz-gNle-mGly-Trp-(N-Me)Nle-Asp(OBZ)-Phe-NH$_2$ in a mixture of 5 cm$^3$ of dimethylformamide and 5 cm$^3$ of methanol, and the mixture is hydrogenated at atmospheric pressure, at a temperature of about 20° C., for 4 hours. After removal of the catalyst by filtration, the filtrate is concentrated to dryness under reduced pressure (1 mm of mercury; 0.13 kPa) at 40° C. 0.23 g of H-gNle-mGly-Trp-(N-Me)Nle-Asp-Phe-NH$_2$ are thus obtained, in the form of a solid white product melting at 138°-140° C.

Rf=0.5 [silica gel; ethyl acetate-pyridine-acetic acid-water (40-20-6-11 by volume)].

Stage 9: Preparation of Boc-Tyr-gNle-mGly-Trp-(N-Me)Nle-Asp-Phe-NH$_2$ 0.12 g of Boc-Tyr-ONp and 0.05 g of HOBt are added to a solution, cooled to 0° C., of 0.2 g of H-gNle-mGly-Trp-(N-Me)Nle-Asp-Phe-NH$_2$ in 3 cm$^3$ of dimethylformamide, and the reaction mixture is stirred for 30 minutes at 0° C., and for 4 hours at a temperature of about 20° C. After evaporation of the solvent under reduced pressure (1 mm of mercury; 0.13 kPa), the oily residue is precipitated with a mixture of ethyl acetate and diethyl ether. 0.173 g of Boc-Tyr-gNle-mGly-Trp-(N-Me)Nle-Asp-Phe-NH$_2$ are thus obtained, in the form of a white solid melting at 162°-164° C.

Rf=0.42 [silica gel; ethyl acetate-pyridine-acetic acid-water (100-20-6-11 by volume)].

Stage 10: Preparation of the desired product: Boc-Tyr(SO$_3$Na)-gNle-mGly-Trp-(N-Me)Nle-Asp-Phe-NH$_2$ 1 g of a sulfur dioxide-pyridine complex are added to a solution of 0.16 g of Boc-Tyr-gNle-mGly-Trp-(N-Me)Nle-Asp-Phe-NH$_2$ in a mixture of 2 cm$^3$ of dimethylformamide and 5 cm$^3$ of pyridine, and the reaction mixture is stirred under a nitrogen atmosphere for one night at a temperature of about 20° C. After evaporation of the solvent under reduced pressure (1 mm of mercury; 0.13 kPa) at 40° C., the residue is taken up at 0° C. in 5 cm$^3$ of water, and the suspension is stirred for 3 hours at 0° C., maintaining the pH at a value of about 7 by means of a saturated aqueous solution of sodium bicarbonate. The suspended product is collected by centrifugation. A second fraction of product is obtained by lyophilization of the aqueous phase and precipitation of the inorganic salts with methanol. These two fractions are pooled and purified by chromatography on a silica gel column, eluting with a mixture of ethyl acetate, pyridine, acetic acid and water (60-20-6-11 by volume). 0.10 g of Boc-Tyr(SO$_3$Na)-gNle-mGly-Trp-(N-Me)Nle-Asp(Na)-Phe-NH$_2$ are thus obtained in the form of a white solid.

Rf=0.26 [silica gel; ethyl acetate-pyridine-acetic acid-water (60-20-6-11 by volume)].

Mass spectrum using FAB ionization: m/e=1150 (MH+).

HPLC: retention time=19 minutes; eluant: mixture of triethylamine phosphate buffer (0.025M; pH=6.5)

and acetonitrile (65-35 by volume); flow rate 1.2 cm³/minute.

Working as indicated in Examples 13 to 15, the following products were prepared using one or other of the routes above:

EXAMPLE 16:
Boc-Tyr(SO₃Na)-Nle-Gly-Trp-(N-Me)Nle-Asp(Na)-Phe-NH₂

Rf: 0.50 [silica gel; ethyl acetate-pyridine-acetic acid-water (40-20-6-11 by volume)].

Mass spectrum using FAB ionization: m/e=1150 (MH+).

HPLC: retention time=28 minutes; eluant: mixture of triethylamine phosphate buffer (0.025M; pH 6.5) and acetonitrile (65-35 by volume); flow rate 1.2 cm³/minute.

EXAMPLE 17:
Boc-Tyr(SO₃Na)-gNle-mGly-Trp-Nle-Asp(Na)-Phe-NH₂

Rf: 0.30 [silica gel; ethyl acetate-pyridine-acetic acid-water (80-20-6-11 by volume)].

Mass spectrum using FAB ionization: m/e=1136 (MH+).

HPLC: retention time=16 minutes; eluant: mixture of triethylamine phosphate buffer (0.025M; pH 6.5) and acetonitrile (65-35 by volume); flow rate 1.2 ml/minute.

EXAMPLE 18:
Ac-L-Phe(p-CH₂SO₃Na)-gNle-mGly-Trp-(N-Me)Nle-Asp-Phe-NH₂

Rf: 0.18 [silica gel; ethyl acetate-pyridine-acetic acid-water (40-20-6-11 by volume)].

Mass spectrum using FAB ionization: m/e=1068 (MH+).

HPLC: retention time=7.2 minutes; eluant: mixture of triethylamine phosphate buffer (0.025M; pH 6.5) and acetonitrile (65-35 by volume).

EXAMPLE 19:
Ac-L-Phe(p-CH₂SO₃Na)-gMet-Gly-Trp-(N-Me)Nle-Asp-Phe-NH₂

Rf: 0.28 [silica gel; ethyl acetate-pyridine-acetic acid-water (40-20-6-11 by volume)].

Mass spectrum using FAB ionization: m/e=1086 (MH+).

HPLC: retention time=16 minutes; eluant: mixture of triethylamine phosphate buffer (0.025M; pH 6.5) and acetonitrile (65-35 by volume).

EXAMPLE 20:
Ac-L-Phe(p-CH₂SO₃Na)-gNle-mGly-Trp-(N-Me)Met-Asp-Phe-NH₂

Rf: 0.15 [silica gel; ethyl acetate-pyridine-acetic acid-water (80-20-6-11 by volume)].

Mass spectrum using FAB ionization: m/e=1086 (MH+).

HPLC: retention time=16 minutes; eluant: mixture of triethylamine phosphate buffer (0.025M; pH 6.5) and acetonitrile (68-32 by volume).

EXAMPLE 21:
Ac-L-Phe(p-CH₂SO₃Na)-gThr-mGly-Trp-(N-Me)Nle-Asp-Phe-NH₂

Rf: 0.23 [silica gel; ethyl acetate-pyridine-acetic acid-water (40-20-6-11 by volume)].

Mass spectrum using FAB ionization: m/e=1056 (MH+).

HPLC: retention time=7 minutes; eluant: mixture of triethylamine phosphate buffer (0.025M; pH 6.5) and acetonitrile (63-37 by volume).

EXAMPLE 22:
Ac-L-Phe(p-CH₂SO₃Na)-gMet-mGly-Trp-(N-Me)-Met-Asp-Phe-NH₂

Rf: 0.17 [silica gel; ethyl acetate-pyridine-acetic acid-water (60-20-6-11 by volume)].

Mass spectrum using FAB ionization: m/e=1104 (MH+).

HPLC: retention time=15.3 minutes; eluant: mixture of triethylamine phosphate buffer (0.025M; pH 6.5) and acetonitrile (63-37 by volume).

EXAMPLE 23: DEMONSTRATION OF THE ACTIVITY OF THE COMPOUNDS FROM EXAMPLES 13 TO 16 AND 18

1) Binding tests:

The cholecystokinin analogs are tested in competition experiments with the ($^3$H)-propionyl-CCK$_8$ ligand on cortex and pancreatic membranes of the guinea pig. The experimental protocols for the preparation of tissues and the binding conditions are analogous to those described by Pelaprat et al., Life Sci., 37, 2489 (1985).

The results are expressed as inhibition constants $K_I$ in Table I which follows. The values shown in this table represent the mean ($\pm$ s.e.m.) of three separate experiments, each being carried out in triplicate. The ($^3$H)-propionyl-CCK$_8$ was used at the concentration corresponding to its dissociation constant, that is to say, 0.2 nM for the brain and 0.1 nM for the pancreas.

TABLE I

| Product tested | Binding test Guinea pig cortex $K_I$ (in M) | Binding test Guinea pig pancreatic membranes $K_I$ (in M) |
| --- | --- | --- |
| Example 13 | $3.2 \pm 0.59 \times 10^{-9}$ | $1.7 \pm 0.2 \times 10^{-9}$ |
| Example 14 | $1.6 \pm 0.21 \times 10^{-8}$ | $1.9 \pm 0.4 \times 10^{-8}$ |
| Example 15 | $0.11 \pm 0.02 \times 10^{-9}$ | $1.06 \pm 0.07 \times 10^{-9}$ |
| Example 16 | $0.15 \pm 0.02 \times 10^{-9}$ | $78 \pm 6 \times 10^{-9}$ |
| Example 18 | $1.3 \pm 0.53 \times 10^{-9}$ | $93 \pm 4 \times 10^{-9}$ |

2) Pancreatic amylase liberation test:

Amylase secretion is measured after incubation of pancreatic acini for 30 minutes at 37° C. in the presence of the products under study, according to the experimental protocol described by Peikin et al., Am. J. Physiol., 235 (6), E 743-E 749, (1978). Amylase activity is determined using Phadebas reagent (Pharmacia), according to the method described by Ceska et al., Experientia, 25, 555 (1969). The results observed are shown in Table II which follows. The values indicated in this table represent the mean of three separate experiments, each carried out in triplicate.

TABLE II

| Product tested | Amylase secretion from guinea pig pancreatic acini Agonist activity EC$_{50}$ (M) |
| --- | --- |
| Example 13 | $3.3 \pm 0.9 \times 10^{-10}$ |
| Example 14 | $1.6 \pm 0.4 \times 10^{-9}$ |
| Example 15 | $0.35 \pm 0.07 \times 10^{-9}$ |
| Example 16 | $377 \pm 118 \times 10^{-9}$ |
| Example 18 | $642 \pm 91 \times 10^{-9}$ |

3) Test for contraction-producing activity on guinea pig ileum

This test is carried out according to the method described by Hutchinson et al., Eur. J. Pharmacol., 69, 87 (1981). Strips from the terminal portion of the guinea pig ileum are rapidly sampled and fixed in the tank of an isometric gauge containing 25 cm³ of Tyrode's solution. The solution is maintained at 37° C. while passing through it, bubble by bubble, a gas composed of 95% oxygen and 5% $CO_2$. The compounds under study are tested in the conditions described by Ruiz-Gayo et al., Peptides, 6, 415, (1985).

The results observed are reported in Table III. The values indicated in this table represent the mean ($\pm$ s.e.m.) of three separate experiments.

TABLE III

| Product tested | Contraction-producing activity on guinea pig ileum Agonist acitivity $EC_{50}$ (M) |
|---|---|
| Example 13 | $3.8 \pm 0.3 \times 10^{-9}$ |
| Example 14 | $1.8 \pm 0.4 \times 10^{-8}$ |
| Example 15 | $1.0 \pm 0.1 \times 10^{-9}$ |
| Example 16 | >1000 |
| Example 18 | >1000 |

EXAMPLE 24: TEST FOR ENZYMATIC STABILITY ON THE COMPOUNDS OF EXAMPLES 15, 16, 18

The resistance of these analogs to enzymatic degradation was tested in crude rat brain membranes which contain at the same time aminopeptidasic, thiolproteasic and encephalinasic activity [Matsas et al. Febs. Lett. 175, 124 (1984); McDermott et al. Neurochem. Int. 5, 641 (1983)]. These compounds were tested according to the protocol previously described by Durieux et al. Neuropeptides 7, 1, (1986). The values obtained (½-life time) are shown in Table IV.

TABLE IV

| Product tested | ½ life time |
|---|---|
| $CCK_8$ | 45 minutes |
| Example 15 | >180 minutes |
| Example 16 | >250 minutes |
| Example 18 | >250 minutes |

EXAMPLE 25

An injectable solution containing 2 mg of active product, and having the following composition, is prepared:

| | |
|---|---|
| Monosodium N-acetyl-4-sulfonatomethyl-phenylalaninate | 2 mg |
| Distilled water qs | 2 cm³ |

EXAMPLE 26

An injectable solution containing 1 mg of active product, and having the following composition, is prepared:

| | |
|---|---|
| Ac—L—Phe(p-$CH_2SO_3Na$)—NLe—Gly—Trp—NLe—Asp—Phe—$NH_2$ | 1.03 mg |
| Distilled water qs | 2 cm³ |

EXAMPLE 27

An injectable solution containing 1 mg of active product, and having the following composition, is prepared:

| | |
|---|---|
| Boc—Tyr($SO_3Na$)—gNle—mGly—Trp—(N—Me)Nle—Asp(Na)—Phe—$NH_2$ | 1 mg |
| Distilled water qs | 2 cm³ |

EXAMPLE 28

An injectable solution containing 1 mg of active product, and having the following composition, is prepared:

| | |
|---|---|
| Al—L—Phe(p-$CH_2SO_3Na$)—gNle—mGly—Trp—(N—Me)Nle—Asp—Phe—$NH_2$ | 1 mg |
| Distilled water qs | 2 cm³ |

We claim:

1. A chemical compound represented by the formula:

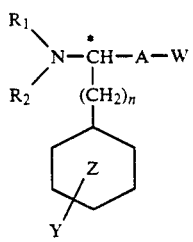

in which:
each of $R_1$ and $R_2$ independently represents a hydrogen atom; a straight- or branched-chain $C_1$-$C_8$ alkyl radical, optionally substituted; a $C_3$-$C_7$ cycloalkyl radical or a mono- or polycyclic aromatic residue, optionally substituted;
in the case in which $R_1$ represents a hydrogen atom, $R_2$ being also capable of representing a radical which protects the amine function, of the acyl type or the urethane type, or even an amino acid residue or a peptide fragment;
$R_1$ and $R_2$ being also capable of forming, with the nitrogen atom to which they are attached, a 5- to 7-component ring capable of containing another heteroatom, and capable of being substituted by a straight- or branched-chain $C_1$-$C_8$ alkyl radical;

A represents —CO

Y represents a residue chosen from those of formula:

$$-OSO_2OR_3 \quad (II);$$

$$-OPO(OR_3)_2 \quad (III);$$

$$-(CH_2)_m-SO_2OR_3 \quad (IV);$$

and $$-(CH_2)_m-PO(OR_3)_2 \quad (V),$$

where
$R_3$ represents a hydrogen atom, a sodium atom or a straight- or branched-chain $C_1-C_8$ alkyl radical, optionally substituted; and
m is from 1 to 4;
Z represents a 6-component ring chosen from the cyclohexane, pyridyl or phenyl rings, optionally substituted; and
n is from 0 to 4;
W represents:

-B-D-Trp-E-Asp-PheNHQ, where:
B and E, which may be identical or different, represent a residue chosen from methionine, norleucine, leucine, serine, threonine, allothreonine, cysteine, homocysteine and the corresponding N-methylated derivatives, the OH or SH functions of serine, threonine, allothreonine, cysteine and homocysteine residues or their corresponding N-methylated derivatives being capable of being free or protected,
D represents a glycine residue;
Q represents hydrogen or a straight- or branched chain $C_1-C_8$ alkyl group, optionally substituted, or even phenyl or phenylalkyl, the alkyl fraction of which has a straight or branched chain and contains 1 to 8 carbon atoms, the phenyl fraction of which can be substituted;
B being capable also of representing a 1,1-diaminoalkyl, 1,1-diaminomethylthioalkyl, 1,1-diaminomercaptoalkyl or 1,1-diaminohydroxyalkyl residue, the alkyl fractions being $C_1-C_8$, with a straight or branched chain, optionally substituted by a cycloalkyl residue or aromatic residue, and, in all cases, D necessarily representing a malonic residue;
on the condition that when Y represents a (II) or (III) residue, the sequence-AW is other than a sequence composed of natural amino acids, the compound being in the D, L or DL form; a mixture thereof as a pharmaceutically acceptable salt thereof.

2. A chemical compound as claimed in claim 1, wherein the radical of the acyl type which protects the amine function, and falls within the definition of $R_2$, is a formyl, acetyl, chloroacetyl, trifluoroacetyl, propionyl, butyryl, isobutyryl, γ-chlorobutyryl, oxalyl, succinyl, glutamyl, pyroglutamyl, phthalyl or p-toluene-sulfonyl radical.

3. A chemical compound as claimed in claim 1, wherein the radical of the urethane type which protects the amine function, and falls within the definition of B is a tertbutyloxycarbonyl, isopropyloxycarbonyl, ethoxycarbonyl, allyloxycarbonyl, benzyloxycarbonyl, mono- or polyhalobenzyloxycarbonyl or nitrobenzyloxycarbonyl radical.

4. A chemical compound as claimed in claim 1, wherein the Z residue is a phenyl residue.

5. A pharmaceutical composition, which contains at least one compound as described in claim 1, in association with one or more diluents or adjuvants which are compatible or pharmaceutically acceptable.

6. A composition as claimed in claim 5, which is intended for the treatment of nervous diseases of central origin, for palliation of the ageing of nervous cells, for the treatment of pain, and is applied as an anorexia-producing agent and as an agent for the stimulation of intestinal motility.

7. A composition according to claim 6 and having an effective amount of the compound.

8. The compound of claim 1, which is Boc-Tyr(SO$_3$Na)-gNle-mGly-Trp-(N-Me)Nle-Asp(Na)-Phe-NH$_2$ or a pharmaceutically-acceptable salt thereof.

9. A chemical compound as claimed in claim 1 wherein Z represents an optionally-substituted cyclohexane ring.

10. A chemical compound as claimed in claim 1 wherein Z represents an optionally-substituted pyridyl ring.

11. A chemical compound according to claim 1 in which $R_1$ is a hydrogen atom; $R_2$ is a radical which protects the amine function of the acyl type or of the urethane type; A is carbonyl; W is -B-D-Trp-E-Asp-PheNHQ; each of B and E is norleucine or its corresponding N-methylated derivative; D is a glycine residue; Q is hydrogen; Z is phenyl ring; Y is a member selected from the group consisting of —OSO$_2$OR$_3$ and —(CH$_2$)$_m$—SO$_2$OR$_3$, and is in the para position; $R_3$ is hydrogen or Na; m is 1; and n is 0 or 1.

12. The chemical compound of claim 11 which is Ac-L-Phe(p-CH$_2$SO$_3$)-NLe-Gly-Trp-NLe-Asp-PheNH$_2$.

13. The chemical compound of claim 11 which is Ac-D-Phe(p-CH$_2$SO$_3$Na)-NLe-Gly-Trp-NLe-Asp-PheNH$_2$.

14. The chemical compound of claim 11 which is Boc-Tyr(SO$_3$Na)-gNle-mGly-Trp-(N-Me)Nle-Asp(Na)-Phe-NH$_2$.

15. The chemical compound of claim 11 which is Boc-Tyr(SO$_3$Na)-Nle-Gly-Trp-(N-Me)Nle-Asp(Na)-Phe-NH$_2$.

16. The chemical compound of claim 11 which is Ac-L-Phe(p-CH$_2$SO$_3$Na)-gNle-mGly-Trp-(N-Me)Nle-Asp-Phe-NH$_2$.

* * * * *

UNITED STATES PATENT AND TRADEMARK OFFICE
CERTIFICATE OF CORRECTION

PATENT NO. : 5,190,921
DATED : March 2, 1993
INVENTOR(S) : ROQUES et al.

It is certified that error appears in the above-identified patent and that said Letters Patent is hereby corrected as shown below:

On the title page, left column at [30], "[JP] Japan ...... 63-10391" should read --[FR] France ...... 88-10391--.

Signed and Sealed this

Sixteenth Day of August, 1994

Attest:

BRUCE LEHMAN

Attesting Officer  Commissioner of Patents and Trademarks